US012569214B2

(12) United States Patent
Menser et al.

(10) Patent No.: US 12,569,214 B2
(45) Date of Patent: Mar. 10, 2026

(54) CONTACTLESS MEASUREMENT AND VISUALIZATION OF RESPIRATION FOR CHEST RADIOGRAPHY IMAGE EXAMINATIONS

(71) Applicant: KONINKLIJKE PHILIPS N.V., Eindhoven (NL)

(72) Inventors: Bernd Menser, Hauset (BE); Julien Thomas Senegas, Hamburg (DE); Sascha Andreas Jockel, Hamburg (DE); Detlef Mentrup, Hamburg (DE); Axel Saalbach, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 184 days.

(21) Appl. No.: 18/280,334

(22) PCT Filed: Mar. 10, 2022

(86) PCT No.: PCT/EP2022/056182
§ 371 (c)(1),
(2) Date: Sep. 5, 2023

(87) PCT Pub. No.: WO2022/194666
PCT Pub. Date: Sep. 22, 2022

(65) Prior Publication Data
US 2024/0065663 A1     Feb. 29, 2024

(30) Foreign Application Priority Data

Mar. 16, 2021     (EP) .................................... 21162888

(51) Int. Cl.
*A61B 6/00*          (2024.01)
*G06T 7/20*          (2017.01)
*G16H 30/40*         (2018.01)

(52) U.S. Cl.
CPC ................ *A61B 6/541* (2013.01); *G06T 7/20* (2013.01); *G16H 30/40* (2018.01); *G06T 2207/10004* (2013.01)

(58) Field of Classification Search
CPC .......... G16H 30/40; A61B 6/541; G06T 7/20; G06T 2207/10004
See application file for complete search history.

(56) References Cited

U.S. PATENT DOCUMENTS 11,311,252 B2 *  4/2022  Jacquel ................ A61B 5/1176
12,016,670 B2 *  6/2024  Vadlamudi-Reddy .......................
                                              G06F 17/142

(Continued)

FOREIGN PATENT DOCUMENTS

CN     105869144 A     8/2016
JP     2005218507 A     8/2005

(Continued)

OTHER PUBLICATIONS

PCT International Search Report, International application No. PCT/EP2022/056182, May 20, 2022.

(Continued)

*Primary Examiner* — David J Makiya
(74) *Attorney, Agent, or Firm* — Larry Liberchuk

(57)          ABSTRACT

The present invention relates to chest radiography. In order to improve image quality and consistency, there is provided a breathing status determination device, which comprises an input unit, a processing unit, and an output unit. The input unit is configured to receive a sequence of depth images that is continuously captured with a sensor having a field of view covering a torso of a patient positioned for a chest radiography image examination. The processing unit is configured to analyse the received sequence of depth images to determine a change of depth values inside one or more region-of-interests (ROIs) overtime that represents a respiratory (Continued)

motion of the patient, and to determine a breathing signal based on the determined change of depth values inside the one or more ROIs over time. The output unit is configured to provide the determined breathing signal.

13 Claims, 5 Drawing Sheets

(56)                    References Cited

U.S. PATENT DOCUMENTS

| | | | |
|---|---|---|---|
| 2005/0201510 A1 | 9/2005 | Mostafavi | |
| 2012/0253178 A1 | 10/2012 | Mostafavi | |
| 2015/0228071 A1 | 8/2015 | Jockel | |
| 2016/0345867 A1 | 12/2016 | Aoki | |
| 2017/0055920 A1 | 3/2017 | Mestha | |
| 2019/0209046 A1* | 7/2019 | Addison | A61B 5/1135 |
| 2020/0202620 A1 | 6/2020 | Kiely | |
| 2022/0047237 A1* | 2/2022 | Liu | A61B 6/032 |
| 2023/0255583 A1* | 8/2023 | Fouras | A61B 6/4014 |

FOREIGN PATENT DOCUMENTS

| | | |
|---|---|---|
| TW | M484407 U | 8/2014 |
| WO | WO2016189071 A1 | 12/2016 |

OTHER PUBLICATIONS

Carmichael J. H. E. et al., "European Guidelines on Quality Criteria for Diagnostic Radiographic Images", Office for Official Publications of the European Communities, 1996.

Senegas J. et al., "Evaluation of Collimation Prediction Based on Depth Images and Automated Landmark Detection for Routine Clinical Chest X-Ray Exams", Medical Image Computing and Computer Assisted Intervention—MICCAI 2018, LNCS, vol. 11071, pp. 571-579, Sep. 2018. https://doi.org/10.1007/978-3-030-00934-2_64.

Penne J. et al., "Robust Real-Time 3D Respiratory Motion Detection Using Time-of-Flight Cameras", International Journal of Computer Assisted Radiology and Surgery, vol. 3 Issue 5, pp. 427-431, 2008.

Brahme A. et al., "4D Laser Camera for Accurate Patient Positioning, Collision Avoidance, Image Fusion and Adaptive Approaches During Diagnostic and Therapeutic Procedures", Medical Physics, AIP, Melville, NY, US, vol. 35, No. 5, Apr. 8, 2008 (Apr. 8, 2008), pp. 1670-1681, XP012116028.

Quoc-Viet T. et al., "Pyramidal Lucas-Kanade-Based Noncontact Breath Motion Detection", IEEE Transactions On Systems, Man, and Cybernetics: Systems, IEEE, Piscataway, NJ, USA, vol. 50, No. 7, Jul. 2020 (Jul. 2020), pp. 2659-2670, XP011793669.

* cited by examiner

200

210

220

230

240

CONTACTLESS MEASUREMENT AND VISUALIZATION OF RESPIRATION FOR CHEST RADIOGRAPHY IMAGE EXAMINATIONS

FIELD OF THE INVENTION

The present invention relates to chest radiography, and in particular to a breathing status determination device, to a chest radiography imaging system, to a method for determining a breathing status of a patient, and to a computer program element.

BACKGROUND OF THE INVENTION

Chest radiography is one of the most important and frequent diagnostic imaging examination. For acquiring a good radiographic image, certain diagnostic requirements and image quality criteria have been defined in international and national guidelines and recommendations. A chest radiography in postero-anterior (PA), antero-posterior (AP), or lateral (LAT) projection should be "performed at full inspiration and with suspended respiration". This is required for a proper visualization and assessment of relevant lung structures in the radiographic image.

In today's workflow, the operator gives a breathing command, usually while leaving the examination room, and afterwards triggers the X-ray image acquisition without any visual feedback on the actual breathing state of the patient. Often enough, the patient does not fully comply with the breathing instructions, for example because the patient cannot understand the breathing command or because the patient is not able to hold his breath long enough. The latter may happen especially if the operator gives the breathing command while in the examination room and needs a few seconds to reach the X-ray release control.

However, a radiography correctly taken at full inspiration facilitates the diagnostic task. Moreover, an image taken at a moment of strong respiratory or other chest motion may be degraded by motion blur.

SUMMARY OF THE INVENTION

There may be a need to improve image quality.

The object of the present invention is solved by the subject-matter of the independent claims, wherein further embodiments are incorporated in the dependent claims. It should be noted that the following described aspects of the invention apply also to the breathing status determination device, to the chest radiography imaging system, to the method for determining a breathing status of a patient, and to the computer program element.

According to a first aspect of the present invention, there is provided a breathing status determination device, which comprises an input unit, a processing unit, and an output unit. The input unit is configured to receive a sequence of depth images that is continuously captured with a sensor having a field of view covering a torso of a patient positioned for a chest radiography image examination. The processing unit is configured to analyse the received sequence of depth images to determine a change of depth values inside at least one region-of-interest (ROI) over time that represents a motion of a patient anatomy orthogonal to an image plane of the sensor and/or a motion of a patient anatomy within the image plane of the sensor, and to determine a breathing signal based on the determined change of depth values inside the at least one ROI over time. The output unit is configured to provide the determined breathing signal.

In other words, it is proposed to make use of a sequence of depth images that is continuously acquired to track a change of depth values inside one or more ROIs on the patient (e.g. on the patient's back, chest, and/or shoulder) to extract the patient's breathing signal. The sequence of depth images comprise a plurality of depth images arranged in time series. Each depth image may also be referred to as image data frame. The extracted breathing signal may be usable to guide or control the triggering of the image acquisition to achieve different levels of automation.

Breathing changes the volume of the patient's thorax and leads to motion of different body parts, e.g. chest/abdomen, shoulders, etc., which is also referred to as breathing motion. Depending on patient orientation (e.g. PA/AP or LAT), these motion vectors could be parallel or orthogonal to the image plane. This is particular to X-ray as opposed to e.g. computed tomography (CT) and magnetic resonance (MR) imaging where there is no flat surface behind the patient. The breathing status determination device as described herein is configured to capture the breathing motion component in the image plane, the breathing motion component orthogonal to the image plane, or both motion components based on the depth camera signal inside one or more ROIs, each ROI covering a particular patient anatomy (e.g. chest, shoulder, etc.).

For example, the sequence of depth images may be acquired by a sensor (e.g., 3D camera) that has an optical axis that is substantially perpendicular to a detector plane defined by a detector front cover or bed. In this geometry setup, the image plane is equal to the detector plane. Further, the respiratory motion may manifest in two ways:

A motion of the patient's back orthogonal to the detector plane (i.e., image plane), leading to a local change of depth values, i.e., z-component of the sensor image (e.g., 3D camera image), and/or An up-and-down motion of the patient's shoulders, i.e. a motion component within the image plane, i.e., y-component of the sensor image (i.e., 3D camera image).

In this way, it is possible to determine a one-dimensional motion component to capture any changes in volume of the subject. There is no need to reconstruct a three-dimensional image of the patient's chest and to produce a real-time measurement of a patient's chest diameter to determine the patient's respiratory motion. Rather, a simple arithmetic average of the depth values inside the at least one ROI or a relative fraction of pixels representing the patient anatomy inside the ROI may be used to determine the patient's respiratory motion.

In an example, the respiratory signal may be displayed to the operator at the console and/or tube head to give feedback on the actual breathing state. The operator is able to check whether the patient is responding to the breathing commands, and releases the x-ray exposure when appropriate.

In another example, the breathing signal may be further analysed and classified, e.g. using a recursive neural network (RNN), and an acoustic and/or visual signal may be given to the operator when a deep inspiration and breathhold is detected.

In a further example, automated gating or triggering of the image acquisition may be performed based on the breathing data acquired in real-time, to acquire the image at a predefined breathing status, like full inhalation. In this level of automation, the operator may enable the image acquisition, e.g. by pressing a button, but the system may delay the actual image acquisition within a predefined time window to find the optimal point in time with respect to breathing state and patient (respiratory) motion. The system delay may be overridden by the user due to clinical demands, e.g. a critical patient condition.

In this way, no wearable sensors need be applied to the patient's body for surveillance of the patient's breathing status during the image acquisition. The patient walks into the examination room "as is" and towards a desired target spot therein. The depth images of the patient's torso are captured with e.g. a range camera, and are then used to detect a motion of one or more ROIs on the patient, which can be used as an indicator of the patient's respiratory signal. Depending on the view of the chest radiography image examination, the one or more ROIs may be defined on the patient's chest, back (PA), chest (AP) shoulder, or a region covering both the patient's torso and the background, which will be explained hereafter and in particular with respect to FIGS. 3 to 7. The patient's breathing signal can thus be derived from a change of depth values inside the one or more ROIs, and are then used to guide or control the triggering of the image acquisition to achieve different levels of automation.

The term "image plane", as used herein, refers to a plane perpendicular to an optical axis of the sensor (e.g., a depth camera), in which a sharp image of object points appears, at least within Gaussian optics. For chest exams, the detector plane, i.e., a plane defined by the detector front cover or bed, is equal to the image plane if the camera is not tilted with respect to the detector normal. For a tilted view (normally not used for chest exams) the detector plane may be different from the image plane. However, anyone of ordinary skill in the art will appreciate that the method as described herein can also be adapted to a tilted view by inducing some non-linear scaling of the breathing signal.

Additionally, the breathing signal provided by the breathing status determination device may be helpful for determining the optimal time point for X-ray release. The patient may benefit in that the number of retakes can be cut down due to an avoidance of motion blur, thereby furthering the ALARA ("As Low As Reasonably Achievable") objective. The radiologists can also enjoy better image quality for the diagnostic task.

According to an embodiment of the present invention, the at least one ROI comprises at least two ROIs including a first ROI and a second ROI. The processing unit is configured to determine a change of depth values inside the first ROI over time that represents a motion of a first patient anatomy orthogonal to the image plane and to determine a change of depth values inside the second ROI over time that represents motion of a second patient anatomy within the image plane. The processing unit is configured to determine a breathing signal based on the determined change of depth values inside both the first and the second ROIs.

In other words, both motion components including a motion component orthogonal to the image plane and a motion component within the image plane could be combined to create a 1D signal that represents the patient's breathing signal. This will be explained in detail hereinafter and in particular with respect to the examples shown in FIG. 4A.

According to an embodiment of the present invention, the at least one ROI comprises an ROI that covers the patient anatomy and a background on both sides of the patient.

Accordingly, the motion of a rigid body does not change to total number of background pixels. Thus, any gross patient motion inside the image plane (often observed in LAT view) does not change the fraction of patient pixels for a wide ROI that includes background on both side of the patient, i.e. does not change the average depth value of such a ROI. Thus, determining a change of depth values inside the ROI that includes patient and static background (e.g. averaging depth values inside the ROI or determining a fraction of patient pixels inside the ROI) can capture any changes in volume and is invariant to a global shift of the subject, i.e. robust to patient motion.

This will be explained in detail hereinafter, and in particular with respect to the examples shown in FIGS. 5A, 5B, 6A, 6B, 7A, and 7B.

According to an embodiment of the present invention, the processing unit is further configured to determine a time point for releasing an x-ray exposure at a pre-defined breathing status based on the determined breathing signal.

For example, the breathing signal may be further analysed and classified, e.g. using a recursive neural network (RNN), to detect a deep inspiration and breath-hold and thus the time point for releasing an x-ray exposure.

Automated gating or triggering of the image acquisition may be performed at the determined time point for releasing an x-ray exposure.

In an example, when the patient is positioned in a posterior-anterior (PA) position for the chest radiography image examination, in a PA view, the at least one ROI comprises an ROI on the patient's back.

In PA view, a motion of the patient's back orthogonal to the detector plane, i.e. image plane, can lead to a local change of depth values. The patient's breathing signal may thus be derived from a change of depth values inside the ROI(s) on the patient's back.

In an example, when the patient is positioned in an anterior-posterior (AP) position for the chest radiography image examination, in an AP view, the one or more ROIs comprise an ROI on the patient's chest.

In AP view, a motion of the patient's chest orthogonal to the image plane can lead to a local change of depth values. The patient's breathing signal may thus be derived from a change of depth values inside the ROI(s) on the patient's chest.

According to an embodiment of the present invention, when the patient is positioned in a lateral position for the chest radiography image examination, in a lateral (LAT) view, the at least one ROI comprises one or more of:

a first ROI comprising pixels representing the patient's back and pixels representing an area in the background;

a second ROI comprising pixels representing the patient's chest and pixels representing an area in the background; and a third ROI on the patient's torso.

The background may be defined by the detector, a bed, system couch, etc.

When the patient is positioned in a lateral position for the chest radiography image examination, the patient breathing cycle may induce a motion of the patient's back, i.e. a motion component within the image plane. This property can be used to extract a breathing signal from an ROI located near the patient's back. The ensemble of depth values inside the ROI are clearly separated into two clusters including the patient's back and the background. The relative fraction of "patient pixels" inside the ROI, which have smaller depth values than the background, changes due to inhalation/exhalation, and can thus be used as an indicator of the patient's respiratory signal. Similar approaches are applicable for the ROI that comprises pixels representing the patient's chest and pixels representing an area in the background.

Another option is to position the ROI on the patient's torso without including any pixels representing the background. During inhalation or exhalation, a motion of the patient's torso orthogonal to the image plane (e.g., the detector plane) can lead to a local change of depth values. Therefore, the patient's breathing signal may be derived from a change of depth values inside the ROI on the patient's torso. This will be explained in detail hereinafter and in particular with respect to the example shown in FIGS. 6A, 6B, 6C, and 6D.

According to an embodiment of the present invention, the at least one ROI comprises an ROI having pixels representing the patient's shoulder and pixels representing an area in the background.

In PA, AP, and LAT view, the respiratory motion can also manifest as an up-and-down motion of the patient's shoulders, i.e. a motion component within the image plane. Therefore, the breathing signal may be derived from an ROI located near the patient's shoulder in PA, AP, and LAT views. In the depth image, the ROI around the detected shoulder landmark includes pixels representing the detector and pixels representing the patient. The ensemble of depth values inside the ROI are clearly separated into two clusters including the patient and the background. The relative fraction of "patient pixels" inside the ROI, which have smaller depth values than the background, changes due to inhalation/exhalation, and may thus be used as an indicator of the patient's respiratory signal.

According to an embodiment of the present invention, the at least one ROI comprises an ROI covering the patient's torso and a background.

In PA view, the ROI may cover both the posterior thorax of the patient and the background (e.g. x-ray detector).

In AP view, the ROI may cover both the anterior thorax and the background (e.g. x-ray detector or examination table).

In LAT view, the ROI may cover the lateral thorax and the background (e.g. x-ray detector or examination table).

The breathing signal deduced from such ROI is robust against rigid patient motion in the image plane. This is beneficial for solving the issue due gross motion of the patient, which will be explained hereafter and in particular with respect to the embodiment shown in FIGS. 7A and 7B.

According to an embodiment of the present invention, the processing unit is configured to determine the at least one ROI based on an active area of an automatic exposure control (AEC) dose measurement chambers or based on one or more anatomical landmarks of the patient.

In an example, if the AEC is used in the majority of examinations, the x-ray technologist has to position the chambers accurately in the patient's lung region, so this area coincides well with the patient's lung position. This will be explained hereafter and in particular with respect to the embodiment shown in FIGS. 2A and 2B.

In another example, the anatomical landmarks may be used to define a patient adaptive ROI for breathing analysis, e.g. by using the bounding box that encompasses the detected lung landmarks. This will be explained hereafter and in particular with respect to the embodiment shown in FIGS. 3A and 3B.

According to an embodiment of the present invention, the processing unit is configured to assess a change of a mean depth value inside the at least one ROI.

For example, a motion component orthogonal to the image plane (e.g. motion of patient's back in PA view) leads to reduced depth values for "patient pixels". Thus, the average of depth values inside ROI reduces.

For example, a motion component in the image plane (e.g. motion of chest in LAT view or vertical shoulder motion in PA view) leads to an increase of the fraction of "patient pixels" compared to pixels representing the background. Thus, the average of depth values inside ROI reduces.

The mean depth value may be a weighted mean or an ordinary mean.

The mean depth value represents a single one-dimensional (1D) time signal and may thus be used as an indicator for the patient's respiratory motion.

According to a second aspect of the present invention, there is provided a chest radiography imaging system that comprises:

an x-ray imaging system with an x-ray source and an x-ray detector spaced from the x-ray source to accommodate a patient to be imaged;

a sensor having a field of view covering a torso of the patient positioned for the chest radiography image examination, wherein the sensor is configured to continuously capture a sequence of depth images of the patient's torso; and a breathing status determination device according to any one of the preceding claims.

For example, the sensor may include a three-dimensional (3D) contactless motion scanner using e.g. light detection and ranging (LIDAR), radio detection and ranging (RADAR), or camera based sensor. The 3D camera based sensor may include e.g. stereo based sensor or infrared video sensor.

In some examples, a single sensor like a range camera is provided. In some examples, multiple sensors may be provided. For example, the depth information may be derived from two or more separate cameras.

The sensor may be either mounted to the x-ray system, e.g. in the tube head, or placed detached from the system, e.g. ceiling mounted.

The sensor (e.g. a range camera) keeps acquiring a sequence of depth image data frames to track a change of depth values inside one or more ROIs on the patient's back, chest, and/or shoulder during inhalation/exhalation, after the patient is positioned for the chest radiography image examination. Based on the change of the depth values inside the one or more ROIs, the patient's breathing signal can be established to guide or control the triggering of the image acquisition with the x-ray imaging system.

The sequence of depth images may be acquired by exposure of the sensor to non-ionizing radiation. For example, infrared light is used but using light in the visible spectrum is also envisaged. The sensor may use a predefined structured light pattern, projected on to the patient to sense the 3D image data. For example, the structured light pattern is a speckle pattern. For example, the sensor may be part of a range camera. Examples are Microsoft Kinect or ASUS Xtion Pro Live equipment.

According to an embodiment of the present invention, the chest radiography imaging system further comprises a feedback device configured to receive a breathing signal from the breathing status determination device and to provide feedback about a breathing status of the patient.

The feedback device may be an auditory feedback device (e.g. speaker), a visual feedback device (e.g. display), or an audio-visual feedback device.

For example, the breathing signal may be displayed in real-time on the operator console. The operator can then visualize the curve and pick the optimal time point for x-ray release.

According to an embodiment of the present invention, the x-ray imaging system is configured to be manually controlled or automatically triggered for an image acquisition at a time point for releasing an x-ray exposure that is determined by the breathing status determination device.

In an example, the breathing signal may be further analysed and classified, e.g. using a recursive neural network (RNN), and an acoustic and/or visual signal is given to the operator when a deep inspiration and breath-hold is detected.

In a further, the operator may enable the image acquisition, e.g. by pressing a button, but the system may delay the actual image acquisition within a predefined time window to find the optimal point in time with respect to breathing state and patient (respiratory) motion. The system delay may be overridden by the user due to clinical demands, e.g. a critical patient condition.

According to a third aspect of the present invention, there is provided a method for determining a breathing status of a patient in a chest radiography image examination that comprises:

receiving a sequence of depth images that is continuously captured with a sensor having a field of view covering a torso of a patient positioned for the chest radiography image examination;

analysing the received sequence of depth images to determine a change of depth values inside at least one region-of-interest, ROI, over time that represents a respiratory motion of the patient;

determining a breathing signal based on the determined change of depth values inside the at least one over time; and providing the determined breathing signal.

According to an embodiment of the present invention, the method further comprises determining a time point for releasing an x-ray exposure at a pre-defined breathing status based on the determined breathing signal.

According to another aspect of the present invention, there is provided a computer program element for controlling a device according to the first aspect and any associated example or for controlling a system according to the second aspect and any associated example, which when being executed by a processor is configured to carry out the method according to the third aspect and any associated example.

These and other aspects of the invention will be apparent from and elucidated with reference to the embodiment(s) described hereinafter.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

DETAILED DESCRIPTION OF EMBODIMENTS

Figure 1:
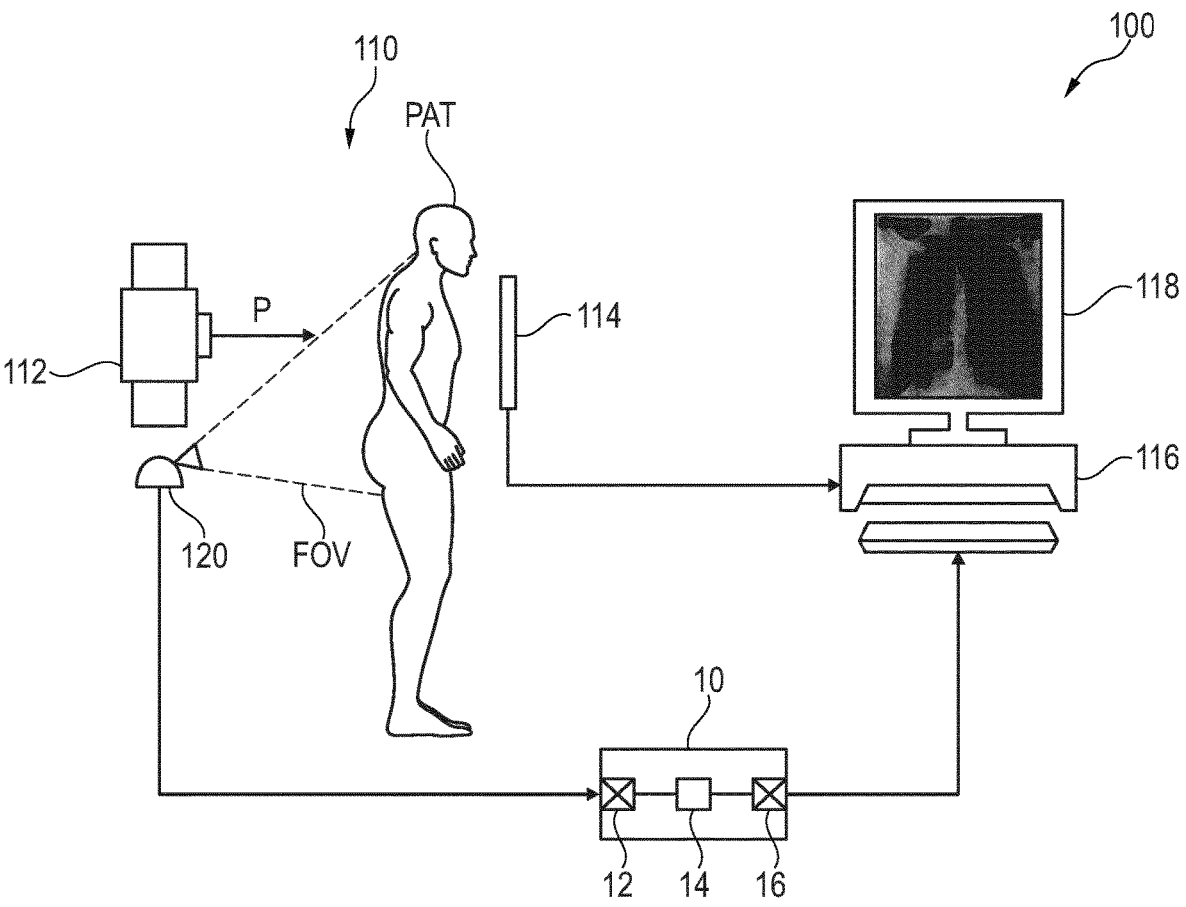
FIG. 1 shows schematically and exemplary a chest radiography imaging system.

FIG. 1 shows schematically and exemplary an embodiment of a chest radiography imaging system 100. The chest radiography imaging system 100 comprises an x-ray imaging system 110, a sensor 120, and a breathing status determination device 10.

The x-ray imaging system 110 comprises an x-ray source 112 and an x-ray detector 114. The x-ray detector 114 is spaced from the x-ray source 112 to accommodate a patient PAT to be imaged.

In general, during an image acquisition, a collimated x-ray beam (indicated with arrow P) emanates from the x-ray source 112, passes through the patient PAT at a region of interest (ROI), experiences attenuation by interaction with matter therein, and the attenuated beam then strikes the surface of the x-ray detector 114. The density of the organic material making up the ROI determines the level of attenuation. That is the rib cage and lung tissue in the chest radiography imaging examination. High density material (such as bone) causes higher attenuation than less dense materials (such as lung tissue). The registered digital values for the x-ray are then consolidated into an array of digital values forming an x-ray projection image for a given acquisition time and projection direction.

Overall operation of the x-ray imaging system 110 may be controlled by an operator from a console 116. The console 116 may be coupled to a screen or monitor 118 on which the acquired x-ray images or imager settings may be viewed or reviewed. An operator such as a medical lab technical can control via the console 116 an image acquisition run by releasing individual x-ray exposures for example by actuating a joy stick or pedal or other suitable input means coupled to the console 116.

In the example of FIG. 1, the patient PAT stands facing a flat surface behind which is the x-ray detector 114. According to a different example (not shown), the x-ray imaging system 110 is of the C-arm type and the patient PAT is actually lying on an examination table instead of standing.

The sensor 120 is configured to continuously capture a sequence of depth images of a torso of the patient positioned for the chest radiography image examination.

For example, the sensor 120 may comprise a range camera with a projector that projects a cone of structured light onto the patient PAT. The cone of structured light may also be referred to as field of view (FOV). Examples of the range camera are Microsoft Kinect or ASUS Xtion Pro Live equipment. The reflection of said light from the patient's surface back to the camera is then registered by the sensor 120 likewise included in the camera. The "distortion" in the reflected speckle pattern is then registered by comparison with how the speckle pattern ought to have looked like had there been no patient present. The registered distortions are then translated into a depth value, also referred to as distance value, for each pixel. It can also be appreciated that the sensor and projector may not necessarily reside in the same camera housing as explained earlier. According to an example, the projector and sensor may be arranged as different components. It is however to be understood that the range camera may also operate according to different principles for example time-of-flight, stereo triangulation, sheet of light triangulation, interferometry and coded aperture.

In another example, the sensor 120 may comprise a stereo camera with two or more lenses with a separate image sensor or film frame for each lens. This allows the camera to simulate human binocular vision, and therefore gives it the ability to capture three-dimensional images, a process known as stereo photography.

In a further example, the depth information may be derived from two or more separate cameras or from a laser scanner.

Other 3D contactless motion scanner using e.g. LIDAR or RADAR may be also suitable for capturing a sequence of depth images of the torso of the patient.

The depth image data can be fused with other sensor data. For example, the depth camera information could be combined with optical flow from the RGB camera channel, or other range data, e.g. from ultrasound (US) sensors.

The sensor 120 may be mounted such that it allows appropriate surveillance of the patient's breathing status.

In the example of FIG. 1, the sensor 120 is mounted near the X-ray tube. In another example (not shown), the sensor 120 may be mounted close to the focal spot, on a ceiling of the examination room, or on a wall of the examination room.

The breathing status determination device 10 may be any computing device, including desktop and laptop computers, smartphones, tablets, etc. The breathing status determination device 10 may be a general-purpose device or a device with a dedicated unit of equipment suitable for providing the below-described functionality. In the example of FIG. 1, the components of the breathing status determination device 10 are shown as integrated in one single unit. However, in alternative examples, some or all components may be arranged as separate modules in a distributed architecture and connected in a suitable communication network. The breathing status determination device 10 and its components may be arranged as dedicated FPGAs or as hardwired standalone chips. In some examples, the breathing status determination device 10 or some of its components may be resident in the console 116 running as software routines.

The breathing status determination device 10 comprises an input unit 12, a processing unit 14, and an output unit 16. Each unit may be part of, or include an Application Specific Integrated Circuit (ASIC), an electronic circuit, a processor (shared, dedicated, or group) and/or memory (shared, dedicated, or group) that execute one or more software or firmware programs, a combinational logical circuit, and/or other suitable components that provide the described functionality.

Broadly speaking, the sensor 120 is configured to acquire a sequence of depth images of the patient PAT by exposure of non-ionizing radiation, e.g. visible light, infrared light, etc. The sequence of depth images captures the 3D shape of the patient or at least the torso part of the patient. Thus, the sequence of the depth images "follows" or describes a change of the outer surface or perimeter of the patient PAT in 3D space for the surveillance of the patient's breathing status.

The sequence of depth images is then fed into the breathing status determination device 10 via the input unit 12, which may be implemented as an Ethernet interface, a USB™ interface, a wireless interface such as a WiFi™ or Bluetooth™ or any comparable data transfer interface enabling data transfer between input peripherals and the processing unit 14. The processing unit 14 then processes the received sequence of depth images in a manner described in more detail below to output a breathing signal, also referred to as respiratory signal, via the output unit 16, which may be implemented as an Ethernet interface, a USB™ interface, a wireless interface such as a WiFi™ or Bluetooth™ or any comparable data transfer interface enabling data transfer between output peripherals and the processing unit 14.

The determined breathing signal may be used to guide or control the triggering of the image acquisition. The following examples describe different possible levels of automation.

In an example, the respiratory signal may be displayed to the operator at the screen 118 coupled to console 116 and/or tube head to give feedback on the actual breathing state. The operator is able to check whether the patient is responding to the breathing commands, and releases the x-ray exposure by actuating a joy stick or pedal or other suitable input means coupled to the console 116, when appropriate.

In another example, the breathing signal is further analysed and classified with the breathing status determination device 10, e.g. using a recursive neural network (RNN). A visual or acoustic guidance may be provided to the operator to inform him about the breathing status, based on the breathing data acquired in real-time.

In a further example, automated gating or triggering of the image acquisition may be performed based on the breathing data acquired in real-time, to acquire the image at a predefined breathing status, like full inhalation. In this example, the operator could for example initiate an X-ray release request, while the system would check the breathing status and would only release exposure for image acquisition if the patient has inhaled and is holding his breath. The user may override the automated gating and release the exposure manually if there is a clinical need.

The following sections describe the determination of the breathing signal from an image sequence registered by the sensor in PA, AP, and LAT views.

Chest Radiography in AP/PA Projection

Posterior-anterior (PA) refers to the direction of the x-ray beam travel, that is, x-ray beams hit the posterior part of the chest before the anterior part. To obtain the image, the patient is asked to stand with their chest against the x-ray detector, to hold their arms up or to the sides and roll their shoulders forward. The x-ray technician may then ask the patient to take few deep breaths and hold it for a couple of seconds. This techniques of holding the breath generally helps to get a clear picture of the heart and lungs on the image.

To obtain antero-posterior (AP) image, the patient is asked to stand with their back against the x-ray detector. If the patient is unable to stand, an AP image can also be taken with the patient sitting or supine on the bed.

In the following, the method is described for the chest radiography in PA projection for the purposes of illustration. However, anyone of ordinary skill in the art will appreciate that the method can also be adapted to the chest radiography in AP projection. The background plane is defined by the detector, a bed, system couch, etc. For ease of reading, the object in the background (e.g. detector) is not illustrated.

In general, respiratory motion generally manifest in two ways:

A motion of the patient's back/chest orthogonal to the detector plane (or image plane), leading to a local change of depth values; and An up-and-down motion of the patient's shoulders, i.e. a motion component within the image plane.

The present disclosure proposes to extract one or both motion components from the sequence of depth images and to obtain a single 1D time signal from the extracted one or both motion components representing the patient's respiratory motion.

For example, the sequence of depth images may be acquired by a sensor (e.g., 3D camera) that has an optical axis that is substantially perpendicular to a detector plane defined by a detector front cover or bed. In this geometry setup, the image plane is equal to the detector plane. Further, the respiratory motion then manifests in the following two ways:

A motion of the patient's back orthogonal to the detector plane (i.e., image plane), leading to a local change of depth values, i.e., z-component of the sensor image (e.g., 3D camera image), and An up-and-down motion of the patient's shoulders, i.e. a motion component within the image plane, i.e., y-component of the sensor image (i.e., 3D camera image).

Details on the signal formation process are given below.

Figure 2A:
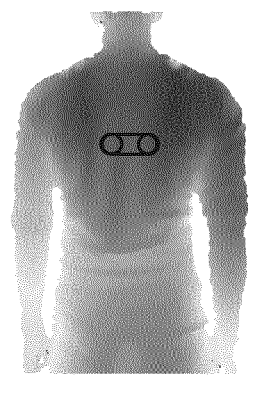
FIG. 2A shows an ROI on the patient's back defined by the active area of the automatic exposure control dose measurement chambers.

In a first option, as shown in FIG. 2A, the one or more ROIs comprise an ROI on the patient's back for extracting a motion of the patient's back orthogonal to the image plane. In this example, the image plane is the detector plane. In the example of FIG. 2A, the ROI is defined on the basis of system geometry parameters, or more specifically by the features representing the x-ray detector in the depth image. For example, the ROI for breathing signal extraction can be defined by the active area of the automatic exposure control (AEC) dose measurement chambers, which may be projected onto the patient surface in the depth image. Since AEC is used in the majority of examinations, the x-ray technologist has to position the chambers accurately in the patient's lung region, so this area coincides well with the patient's lung position.

Figure 2B:
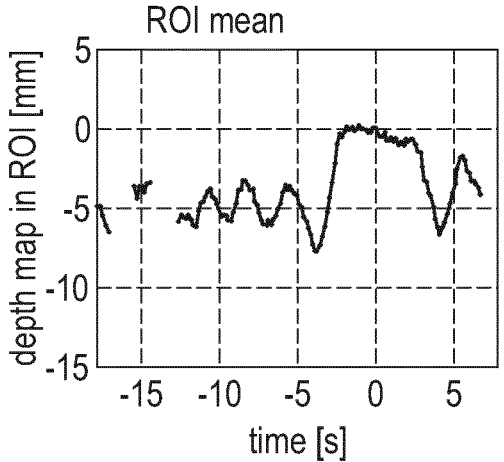
FIG. 2B shows a breathing signal derived from the ROI shown in FIG. 2A.

The processing unit 14 then determines a change of depth values inside the ROI as a function of time that represents a respiratory motion of the patient, and determines a breathing signal based thereon. FIG. 2B shows an example of the breathing signal with deep inspiration and breath-hold, which is extracted from the ROI shown in FIG. 1A. In this example, the 1D breathing signal is created by averaging the depth values inside the ROI. Further processing by temporal filtering, e.g. linear filters or a Kalman Filter, may be applied to suppress outliers and generate a more smoothed time signal. The x-ray image is acquired at t=0.

Figure 3A:
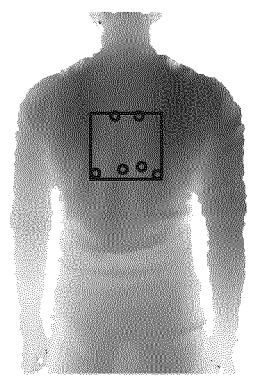
FIG. 3A shows an ROI on the patient's back defined by anatomical landmarks of the patient.

In a second option, as shown in FIG. 3A, the ROI is defined by one or more anatomical landmarks of the patient in the depth image. For example, the processing unit 14 may be configured to estimate the position of external landmarks (e.g. shoulders) or internal landmarks (e.g. lung apex) from a depth image. See for example J. Sénégas, A. Saalbach, M. Bergtholdt, S. Jockel, D. Mentrup, R. Fischbach. Evaluation of Collimation Prediction Based on Depth Images and Automated Landmark Detection for Routine Clinical Chest X-Ray Exams. In: A. F. Frangi et al. (eds.): MICCAI 2018, LNCS 11071, pp. 571-579, Springer, Cham (2018). These landmarks can be used to define a patient adaptive ROI for breathing analysis, e.g. by using the bounding box that encompasses the detected lung landmarks. For example, for a thorax or chest x-ray, hip joints and shoulder joints may be identified from the depth values making up the depth images and the line joining the two hip joints may be used as a lower demarcation for the ROI. The line joining shoulder joints may be used as the upper demarcation with two torso flanks forming the lateral demarcation.

Figure 3B:
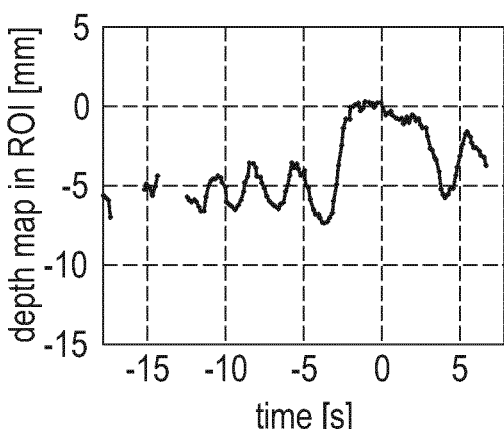
FIG. 3B shows a breathing signal derived from the ROI shown in FIG. 3A.

FIG. 3B shows an example of the breathing signal with deep inspiration and breath-hold, which is extracted from the ROI shown in FIG. 3A. In this example, the 1D breathing signal is also created by averaging the depth values inside the ROI. The X-ray image is acquired at t=0.

Figures 4A, 4B, 5A, 5B:
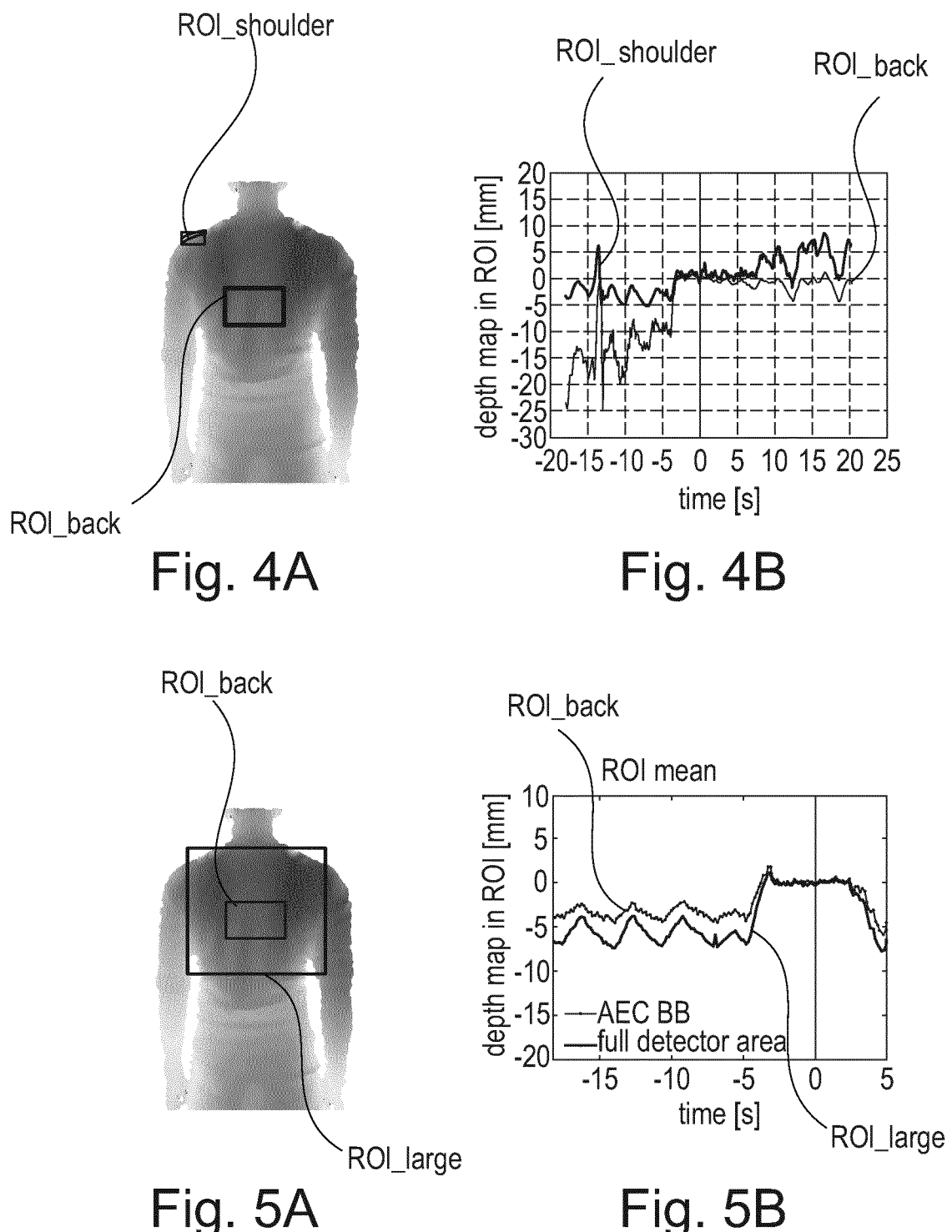
FIG. 4A shows an ROI located near the patient's shoulder.
FIG. 4B shows a breathing signal derived from the ROI shown in FIG. 4A.
FIG. 5A shows an ROI covering both the posterior thorax of the patient and the background.
FIG. 5B shows a breathing signal derived from the ROI shown in FIG. 5A.

In an third option, as shown in FIG. 4A, the patient breathing cycle may also induce a vertical shoulder motion, i.e. a motion component within the image plane. This property can be used to extract a breathing signal from an ROI (shown as ROI_shoulder) located near the patient's shoulder. For example, the landmark detector algorithm may be used to detect shoulder landmarks. In the depth image, the ROI around the detected shoulder landmark includes pixels representing the detector, and pixels representing the patient. The ensemble of depth values inside the ROI are clearly separated into two clusters including patient and background (e.g. x-ray detector or examination table).

FIG. 4B shows an example of the breathing signal with deep inspiration and breath-hold, which is extracted from the ROI shown in FIG. 4A. The processing unit 14 is configured to average all depth values inside the ROI that comprise the region around the detected shoulder landmark. During an upward shift of the shoulder due to inhalation, the relative fraction of "patient pixels" inside the ROI, which all have smaller depth values than the detector, increases. Consequently, the average ROI depth value decreases. Similarly, during exhalation, the average ROI depth value increases. Hence, the average ROI depth value signals is an indicator of the respiratory motion.

FIG. 4A also shows a further ROI (shown as ROI_back) positioned on the patient's back region. The breathing signal extracted from the further ROI is shown in FIG. 4B. In some examples, the two breathing signals shown in FIG. 4B may be combined to compute an optimal breathing signal.

Optionally, the vertical position of the transition between patient and background region may be tracked. Inhalation leads to an upwards shift of the vertical position of this transition, while exhalation results in a downwards shift. Thus, the vertical position of the shoulder/background transition constitutes a 1D signal representing the patient's breathing motion.

As discussed above, respiratory motion can manifest in two types of local image changes: a) a motion component towards the sensor, i.e. orthogonal to the image plane, e.g. the motion of the patient's back in PA view or the motion of the patient's chest in AP view; and b) motion component in the image plane, e.g. the up- and down-movement of the shoulders in PA or AP view.

As discussed already before, the motion component orthogonal to the image plane may be determined according to the first and second options, while the motion component in the image plane may be determined using the third option. Both motion components can be assessed by averaging depth pixels inside an appropriately selected local ROI and subsequently combined, e.g. using a linear combination of the two signals. The average of all depth values inside the ROI will decrease as the patient inhales.

In a fourth option, as shown in FIG. 5A, both motion components can be also jointly accessed by selecting a large ROI (shown as ROI_large), which covers both the patient's torso and part of background, i.e., a background on both sides of the patient. FIG. 5A shows an example of the larger ROI. During the inhalation phase, the lung volume and therefore the volume of the torso increases, which increases the number of "patient pixels" compared to background pixels, and decreases the depth value of the patient pixels.

As shown below, the relative changes of the average depth values inside the ROI after offset correction approximate the relative changes of the patient volume inside the ROI. The average depth signal $\bar{d}(t)$ depends on the average "patient thickness" $\bar{d}_p(t)$, the number of "patient pixels" $N_p$, the distance D of the detector to the sensor, and the total number of pixels N in the ROI:

$$\bar{d}(t)=N_p\cdot(D-\bar{d}_p(t))+(N-N_p(t))\cdot D.$$

The relative changes $x(t)/x(0)$ of the offset corrected signal $$x(t)=\bar{d}(t)-N\cdot D=N_p(t)\cdot\bar{d}_p(t)$$

are directly proportional to the relative changes of the volume $V_p$ w.r.t the x-ray acquisition frame (t=0):

$$\frac{x(t)}{x(0)}=\frac{N_p(t)}{N_p(0)}\cdot\frac{\bar{d}_p(t)}{\bar{d}_p(0)}=\frac{A_p(t)}{A_0(t)}\cdot\frac{\bar{d}_p(t)}{\bar{d}_p(0)}\approx\frac{V_p(t)}{V_0(t)}$$

Thus, the relative changes of the offset corrected signal x approximate the volume changes of the patients torso. This assumes that the volume $V_p$ can be approximated by the product of mean patient thickness $\bar{d}_p$ and patient area $A_p$ e.g. with a cuboid model.

FIG. 5B shows a breathing signal derived from the larger ROI by averaging the depth values inside the ROI. The x-ray image is acquired at t=0.

For comparison, FIG. 5A also shows an ROI (shown as ROI_back) on the patient's back and FIG. 5B shows the breathing signal derived therefrom.

Breathing signal from the large ROI is robust against rigid patient motion in the image plane, which will be explained hereafter and in particular with respect to the embodiment shown in FIGS. 7A and 7B.

Chest Radiography in LAT Projection

The above-described approaches may also be applicable for the lateral projection, possibly requiring an additional sensor and/or a different sensor position, which will be explained hereafter.

A lateral image is usually taken to complement the frontal view. A lateral image is useful to localise a lesion since, together with a frontal image, it allows a three-dimensional analysis. To obtain a lateral image, the patient is asked to turn and place one shoulder on the plate and raise their hands over their head. The technician may again ask the patient to take a deep breath and hold it.

Figures 6A, 6B:
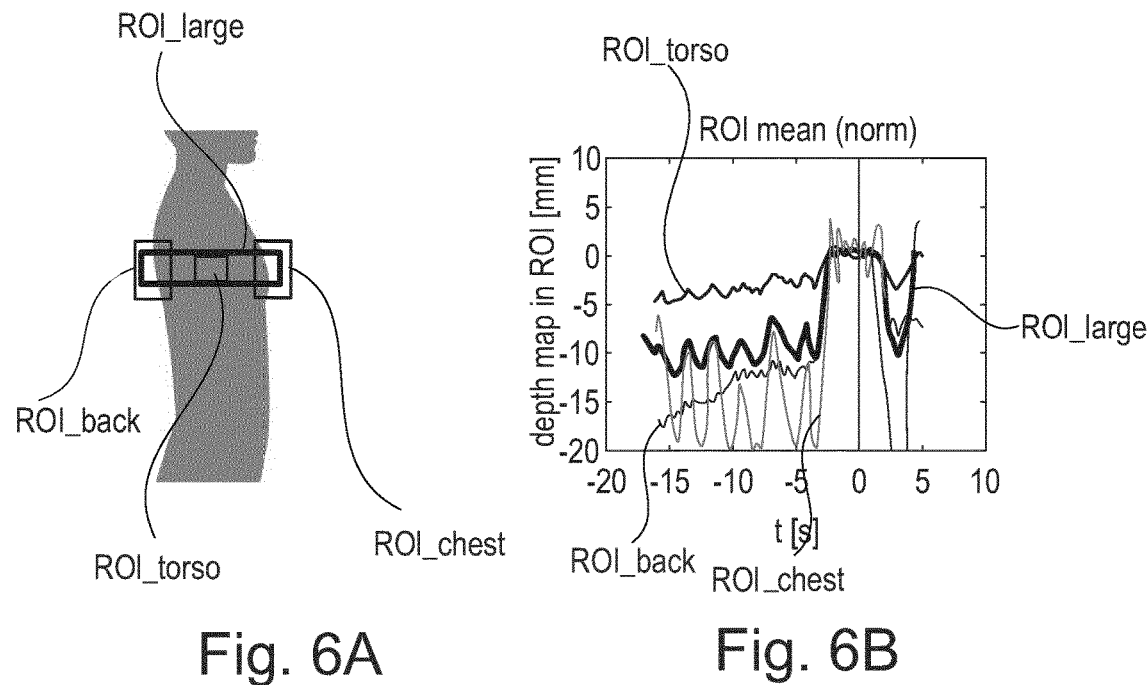
FIG. 6A shows different ROIs that jointly capture breathing motion within and orthogonal to the image plane.
FIG. 6B shows breathing signals derived from the ROIs shown in FIG. 6A.

In LAT view, the one or more ROIs may comprises one or more of the ROIs shown in FIG. 6A.

A first ROI (shown as ROI_back) may comprise pixels representing the patient's back and pixels representing an area in the background (x-ray detector or examination bed). The ensemble of depth values inside the ROI are clearly separated into two clusters including patient's back and background. In this option, the processing unit 14 is configured to average all depth values inside the ROI that comprise the region around the chest. During inhalation, the relative fraction of "patient pixels" inside the ROI, which all have smaller depth values than the background, increases. Consequently, the average ROI depth value decreases. Similarly, during exhalation, the average ROI depth value increases. Hence, the average ROI depth value signals is an indicator of the respiratory motion.

A second ROI (shown as ROI_chest) may comprise pixels representing the patient's chest and pixels representing an area in the background. Similarly, the average ROI depth value signals is an indicator of the respiratory motion.

A third ROI (shown as ROI_torso) may be positioned on the patient's torso. The relative changes of the average depth values inside the ROI is an indicator of the respiratory motion.

A fourth ROI (shown as ROI_large) may be a large ROI that covers the patient's torso and part of in the background by going over a borderline between the patient's chest and the background and by going over a borderline between the patient's back and the background—that is, the fourth ROI covers patient's torso and the background on both sides of the patient.

FIG. 6B shows breathing signals derived from the depth values inside these different ROIs. The x-ray image is acquired at t=0.

Figures 7A, 7B:
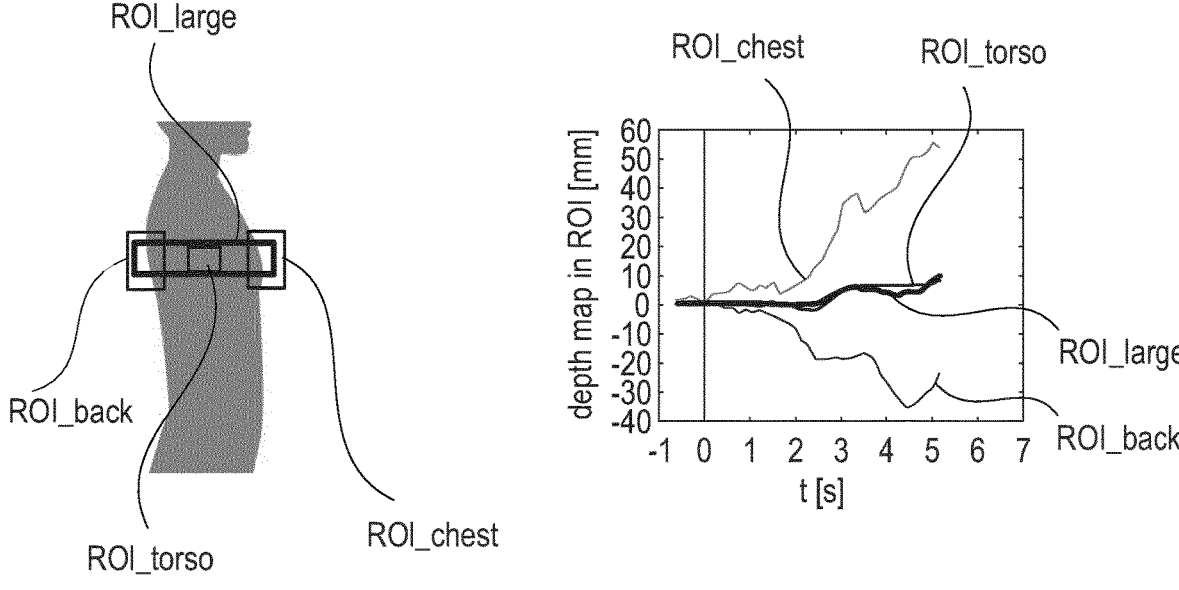
FIG. 7A shows different ROIs that jointly capture breathing motion within and orthogonal to the image plane.
FIG. 7B shows breathing signals derived from the ROIs shown in FIG. 7A, when rigid patient motion occurs.

The breathing signal from the large ROI is robust towards rigid patient motion in the image plane, which frequently occur in LAT exams as shown in FIGS. 7A and 7B. As can be seen from FIG. 7B, the breathing signal derived from the large ROI (shown as ROI_large) is robust against rigid patient motion in the image plane, while the individual signals from the ROIs on the patient's back and chest is corrupted by a gradient due to patient motion.

The determined breathing signal shown in FIGS. 2B to 7B may be further analysed by the processing unit 14 to determine a time point for releasing an x-ray exposure at a pre-defined breathing status based on the determined breathing signal.

For example, the breathing signal may be further analysed and classified, e.g. using a recursive neural network (RNN). RNN is a type of neural networks that is usually applied to the signal, which has a correlation between its values during the time. Fundamentally, an RNN is a looped-back architecture of interconnected neurons and current input whereby the last hidden state affects the output of the next hidden state. An RNN is ideally suited to sequential information and is suitable for time-series data because it also has memory.

During training, different parameters of the networks and layers are explored using the training data set that comprises a plurality of previously recorded patient's breathing signals. The previously recorded patient's breathing signals may be obtained from the same patient and/or from other patient's. The time points for releasing an x-ray exposure at a pre-defined breathing status in the data set may be annotated by expert technicians. After training, the RNN is used to extract temporal features, i.e. time point for releasing an x-ray exposure, from the received breathing signal.

The x-ray imaging system may be manually controlled or automatically triggered for an image acquisition at the determined time point. For example, the operator could for example initiate an x-ray release request, while the system would check the breathing status and would only release exposure for image acquisition at the determined time point. The user may override the automated gating and release the exposure manually if there is a clinical need.

The above-described breathing status determination device 10 and the chest radiography imaging system 100 can readily be adapted to operate for example in a C-arm x-ray imager where the patient PAT is to lie on an examination table during the image acquisition rather than to stand as shown in FIG. 1.

Figure 8:
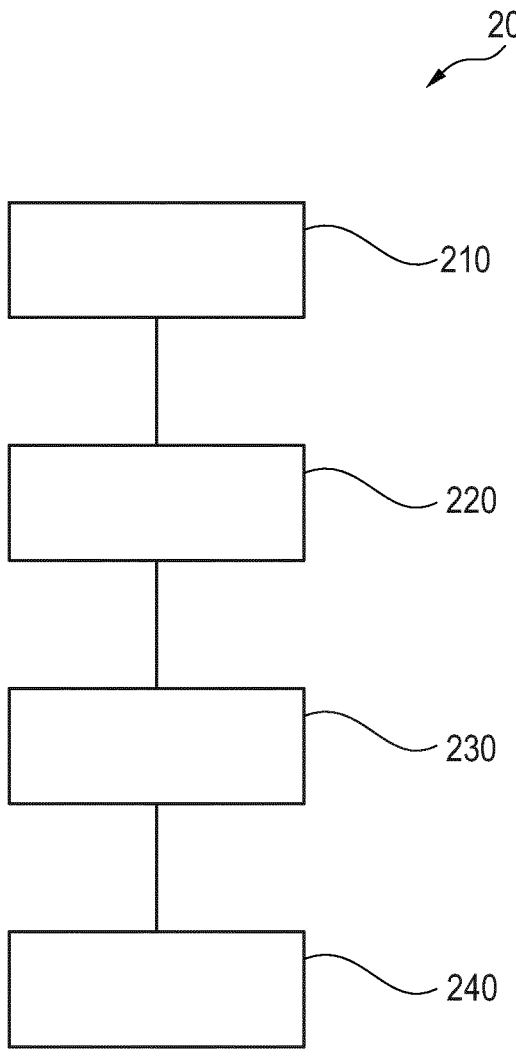
FIG. 8 shows a flow chart of a method for determining a breathing status of a patient in a chest radiography image examination.

With reference to FIG. 8, a flow chart is shown for a method for determining a breathing status of a patient in a chest radiography image examination.

In step 210, a sequence of depth images is received that is continuously captured with a sensor having a field of view covering a torso of a patient positioned for the chest radiography image examination. Thus, once the patient is positioned for the chest radiography image examination, the sensor (e.g. a range camera) keeps acquiring a sequence of depth image data frames of the patient's torso for a prolonged period. The acquired sequence of depth image data frames may be fed into a breathing status determination device 10 shown in FIG. 1 via the input unit 12.

In step 220, the received sequence of depth images is analysed to determine a change of depth values inside one or more region-of-interests (ROIs) over time that represents a respiratory motion of the patient. To put it another way, the depth values inside one or more ROIs may be recorded across the sequence of the individual depth images, and a change of the depth values can be established as a function time.

In step 230, a breathing signal is determined based on the determined change of depth values inside the one or more ROIs over time. For example, a 1D breathing signal may be created by averaging the depth values inside the one or more ROIs by using a weighted mean or an ordinary mean.

In step 240, the determined breathing signal is output, e.g. to a display at the console and/or tube head to give feedback on the actual breathing state. The operator is able to check whether the patient is responding to the breathing commands, and releases the x-ray exposure when appropriate.

Optionally, the breathing signal may be further analysed and classified, e.g. using a recursive neural network (RNN).

In an example, an acoustic and/or visual signal may be given to the operator when a deep inspiration and breath-hold is detected.

In an example, a time point for releasing an x-ray exposure at a pre-defined breathing status may be determined based on the determined breathing signal. The operator could for example initiate an x-ray release request, while the system would check the breathing status and would only release exposure for image acquisition at the determined time point. The user may override the automated gating and release the exposure manually if there is a clinical need.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfil the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium, such as an optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A breathing status determination device, comprising:
an input configured to receive depth images continuously captured with a sensor having a field of view covering a torso of a patient positioned for a chest radiography image examination;

a processor configured to analyze the received depth images to determine a change of depth values inside at least one region-of-interest (ROI) over time that represents a motion of a patient anatomy orthogonal to an image plane of the sensor and/or a motion of a patient anatomy within the image plane of the sensor, wherein the at least one ROI comprises at least two ROIs including a first ROI and a second ROI, wherein the processor is configured to determine a change of depth values inside the first ROI over time that represents a motion of a first patient anatomy orthogonal to the image plane and to determine a change of depth values inside the second ROI over time that represents motion of a second patient anatomy within the image plane, and wherein the processor is configured to determine a breathing signal based on the determined change of depth values inside the first and the second ROIs; and
an output configured to provide the determined breathing signal.

2. The device according to claim 1, wherein the processor is configured to determine a change of a mean depth value inside the at least one ROI to determine the breathing signal.

3. The device according to claim 1, wherein the at least one ROI comprises an ROI that covers the patient anatomy and a background on both sides of the patient.

4. The device according to claim 1, wherein when the patient is positioned in a lateral position for the chest radiography image examination, the at least one ROI comprise:
a first ROI comprising pixels representing the patient's back, and pixels representing an area in a background;
a second ROI comprising pixels representing the patient's chest, and pixels representing an area in a background; and
a third ROI on the patient's torso.

5. The device according to claim 1, wherein the at least one ROI comprises an ROI having pixels representing the patient's shoulder and pixels representing an area in a background.

6. The device according to claim 1, wherein the at least one ROI comprises an ROI covering the patient's torso and a background.

7. The device according to claim 1, wherein the processor is configured to determine the at least one ROI based on an active area of an automatic exposure control (AEC) dose measurement chambers or based on one or more anatomical landmarks of the patient.

8. The device according to claim 1, wherein the processor is further configured to determine a time point for releasing an x-ray exposure at a pre-defined breathing status based on the determined breathing signal.

9. A system, comprising:
an x-ray imaging system comprising an x-ray source and an x-ray detector spaced from the x-ray source to accommodate a patient to be imaged;
a sensor having a field of view covering a torso of the patient positioned for a chest radiography image examination, wherein the sensor is configured to continuously capture depth images of the patient's torso; and
a breathing status determination device comprising:
an input configured to receive depth images continuously captured with a sensor having a field of view covering a torso of a patient positioned for a chest radiography image examination;
a processor configured to analyze the received depth images to determine a change of depth values inside at least one region-of-interest (ROI) over time that represents a motion of a patient anatomy orthogonal to an image plane of the sensor and/or a motion of a patient anatomy within the image plane of the sensor, wherein the at least one ROI comprises at least two ROIs including a first ROI and a second ROI, wherein the processor is configured to determine a change of depth values inside the first ROI over time that represents a motion of a first patient anatomy orthogonal to the image plane and to determine a change of depth values inside the second ROI over time that represents motion of a second patient anatomy within the image plane, and wherein the processor is configured to determine the breathing signal based on the determined change of depth values inside the first and the second ROIs; and
an output configured to provide the determined breathing signal.

10. The system according to claim 9, further comprising:
a feedback device configured to receive a breathing signal from the breathing status determination device, and to provide feedback about a breathing status of the patient.

11. The system according to claim 9, wherein the x-ray imaging system is configured to be manually controlled or automatically triggered for an image acquisition at a time point for releasing an x-ray exposure that is determined by the breathing status determination device.

12. A method for determining a breathing status of a patient in a chest radiography image examination, comprising:
receiving depth images continuously captured with a sensor having a field of view covering a torso of a patient positioned for the chest radiography image examination;
analyzing, by a processor, the received depth images to determine a change of depth values inside at least one region-of-interest (ROI) over time that represents a motion of a patient anatomy orthogonal to an image plane of the sensor and/or a motion of a patient anatomy within the image plane of the sensor, wherein the at least one ROI comprises at least two ROIs including a first ROI and a second ROI, wherein the processor is configured to determine a change of depth values inside the first ROI over time that represents a motion of a first patient anatomy orthogonal to the image plane and to determine a change of depth values inside the second ROI over time that represents motion of a second patient anatomy within the image plane;
determining a breathing signal based on the determined change of depth values inside the first and the second ROIs; and
providing the determined breathing signal.

13. The method according to claim 12, further comprising:
determining a time point for releasing an x-ray exposure at a pre-defined breathing status based on the determined breathing signal.

* * * * *